(12) United States Patent
LeRoy et al.

(10) Patent No.: US 10,383,641 B2
(45) Date of Patent: Aug. 20, 2019

(54) FLEXIBLE AND FLUTED CUTTING DEVICE

(71) Applicant: CLARIANCE, Beaurains (FR)

(72) Inventors: Jean Yves LeRoy, Campagne-les-Hesdin (FR); Adrien Billon, Achicourt (FR); Sebastien Schuller, Strasbourg (FR); Guy Viart, Saint Leger (FR); Nicolas Virgaux, Paris (FR)

(73) Assignee: Clariance, Beaurains (FR)

( * ) Notice: Subject to any disclaimer, the term of this patent is extended or adjusted under 35 U.S.C. 154(b) by 218 days.

(21) Appl. No.: 15/407,880

(22) Filed: Jan. 17, 2017

(65) Prior Publication Data

US 2017/0202563 A1    Jul. 20, 2017

Related U.S. Application Data

(60) Provisional application No. 62/280,315, filed on Jan. 19, 2016.

(30) Foreign Application Priority Data

Jan. 18, 2016  (FR) ..................................... 16 50369

(51) Int. Cl.
*A61B 17/16*   (2006.01)
*A61B 17/00*   (2006.01)
*A61B 90/00*   (2016.01)

(52) U.S. Cl.
CPC ...... *A61B 17/1631* (2013.01); *A61B 17/1615* (2013.01); *A61B 17/1642* (2013.01); *A61B 17/1671* (2013.01); *A61B 2017/00867* (2013.01); *A61B 2090/031* (2016.02)

(58) Field of Classification Search
CPC ............ A61B 17/1631; A61B 17/1615; A61B 17/1637; A61B 17/164; A61B 17/1642; A61B 17/1633; A61B 7/1664; A61B 17/1671

See application file for complete search history.

(56) References Cited

U.S. PATENT DOCUMENTS

| 2007/0093840 | A1* | 4/2007 | Pacelli | A61B 17/1631 606/80 |
| 2009/0326538 | A1* | 12/2009 | Sennett | A61B 17/1617 606/80 |
| 2010/0268234 | A1* | 10/2010 | Aho | A61B 17/1617 606/80 |
| 2013/0345765 | A1* | 12/2013 | Brockman | A61B 17/8855 606/86 R |
| 2014/0171948 | A1* | 6/2014 | Griffiths | A61B 17/1637 606/80 |
| 2015/0038970 | A1* | 2/2015 | Coope | A61B 17/162 606/80 |

(Continued)

*Primary Examiner* — Matthew J Lawson
(74) *Attorney, Agent, or Firm* — Young & Thompson

(57) ABSTRACT

The flexible and fluted cutting device for drilling and/or milling a space in bone tissue or connective tissue includes, on the one hand, a cutting element (2) made up of a rigid tube (20) secured at one of its ends to a supple and flexible connection (21) extended by a fluted cutter (22) and at the opposite end to drive element provided with a safety connector (23) for uncoupling the cutting device and, on the other hand, a guide element (3) providing the positioning and angular deformation of the cutting element (2) within the bone tissue or connective tissue.

19 Claims, 6 Drawing Sheets

(56) References Cited

U.S. PATENT DOCUMENTS

2015/0141998 A1\* 5/2015 Kiapour ............. A61B 17/1642
                                                        606/80
2016/0302936 A1\* 10/2016 Billon ................ A61B 17/1642
2017/0354423 A1\* 12/2017 Piccirillo ........... A61B 17/1631

\* cited by examiner

FLEXIBLE AND FLUTED CUTTING DEVICE

FIELD OF THE INVENTION

The present invention relates to a flexible and fluted cutting device for drilling and/or milling a space in bone tissue or connective tissue.

BACKGROUND OF THE INVENTION

A flexible drill bit comprising a proximal shank part for connection to a rotational-drive device, a distal part made up of a cutting tip that allows bone tissue to be drilled; and an intermediate shaft part extending between the proximal shank part and the distal part is known from the anterior patent US2013/0261628 of Jan. 7, 2013. The intermediate shaft part has, on the one hand, enough longitudinal suppleness to allow the drill bit to deform along a radius of curvature and, on the other hand, enough torsional strength to allow the drill bit to drill a hole in bone tissue.

A flexible shaft used for drilling a bore in bone tissue is also known, from the anterior U.S. Pat. No. 6,053,922 of Jul. 17, 1996. The flexible shaft is made up of a tubular element having an internal longitudinal bore over the entire length of said element and a suitably shaped flute which extends in a continuous spiral or in continuous segments around said tubular element. The tubular element comprises, at each opposite end of the shaft, on the one hand a cutting head and on the other hand a means of connection to a drive device.

It may be noted that the drilling devices of the prior art do not allow the intervertebral space situated between two vertebrae of a segment of spine to be drilled and milled by going through the pedicles of these vertebrae.

This is because the drilling devices of the prior art only drill into bone tissue in a substantially curved direction with no possible control over said radius of curvature and with no guarantee of the drilling point.

SUMMARY OF THE INVENTION

The flexible and fluted cutting device for drilling and/or milling a space in bone tissue or connective tissue according to the present invention, comprises, on the one hand, a cutting element made up of a rigid tube secured at one of its ends to a supple and flexible connection extended by a fluted cutter and at the opposite end to drive means provided with a safety connector for uncoupling said cutting device and, on the other hand, a guide element providing the positioning and angular deformation of the cutting element within the bone tissue or connective tissue.

The flexible and fluted cutting device according to the present invention comprises a cutting element of which the supple and flexible connection is made up of a hollow strand with helicoidal fibers or threads around which a protective sheath is arranged, these being respectively assembled with the fluted cutter on the one hand and with the rigid tube on the other.

The flexible and fluted cutting device according to the present invention comprises a hollow strand which is made up of an arrangement of at least three layers of helicoidal fibers or threads arranged in a staggered configuration delimiting an internal bore.

The flexible and fluted cutting device according to the present invention comprises a hollow strand of which each layer is formed of at least eighteen fibers or threads arranged evenly at the circular periphery of said strand in a helical profile along the longitudinal axis of said strand.

The flexible and fluted cutting device according to the present invention comprises a hollow strand of which the first and third layers are arranged along the longitudinal axis of said strand in one and the same first helical direction, whereas the second layer interposed between the first and the third is directed in a second helical direction that intersects said first helical direction.

The flexible and fluted cutting device according to the present invention comprises a hollow strand which is fixed at one of its ends to the vertical edge of a first cylindrical part of a tubular spacer secured to the rigid tube whereas the other end is assembled with the vertical edge of a shoulder of the fluted cutter.

The flexible and fluted cutting device according to the present invention comprises a supple and flexible connection of which the protective sheath is made up of a spring with contiguous turns enveloping the external face of the helicoidal fibers or threads of the hollow strand and of which each end is respectively secured to the rigid tube and to the fluted cutter.

The flexible and fluted cutting device according to the present invention comprises a supple and flexible connection of which the protective sheath is formed of a supple polymer sheath of which each end is fixed to the rigid tube and the fluted cutter.

The flexible and fluted cutting device according to the present invention comprises a flexible cutting element of which the fluted cutter has at least three teeth evenly distributed about an internal bore and of which the cutting profile respectively removes waste material causing, as said cutting device is rotationally driven, it to advance into the bone tissue or connective tissue.

The flexible and fluted cutting device according to the present invention comprises a flexible cutting element of which the safety connector is secured to the rigid tube via a pin rated to break under a torque which is lower than that of the supple and flexible connection to said rigid tube.

The flexible and fluted cutting device according to the present invention comprises a guide element which is made up of a rod made of Nitinol having a small diameter and an end with a curved profile of predetermined radius ending in a tapered point.

BRIEF DESCRIPTION OF THE DRAWINGS

The description which will follow with reference to the attached drawings given by way of nonlimiting examples will allow a better understanding of the invention, of the features it offers and of the advantages it is likely to afford.

DETAILED DESCRIPTION OF THE INVENTION

Figure 1:
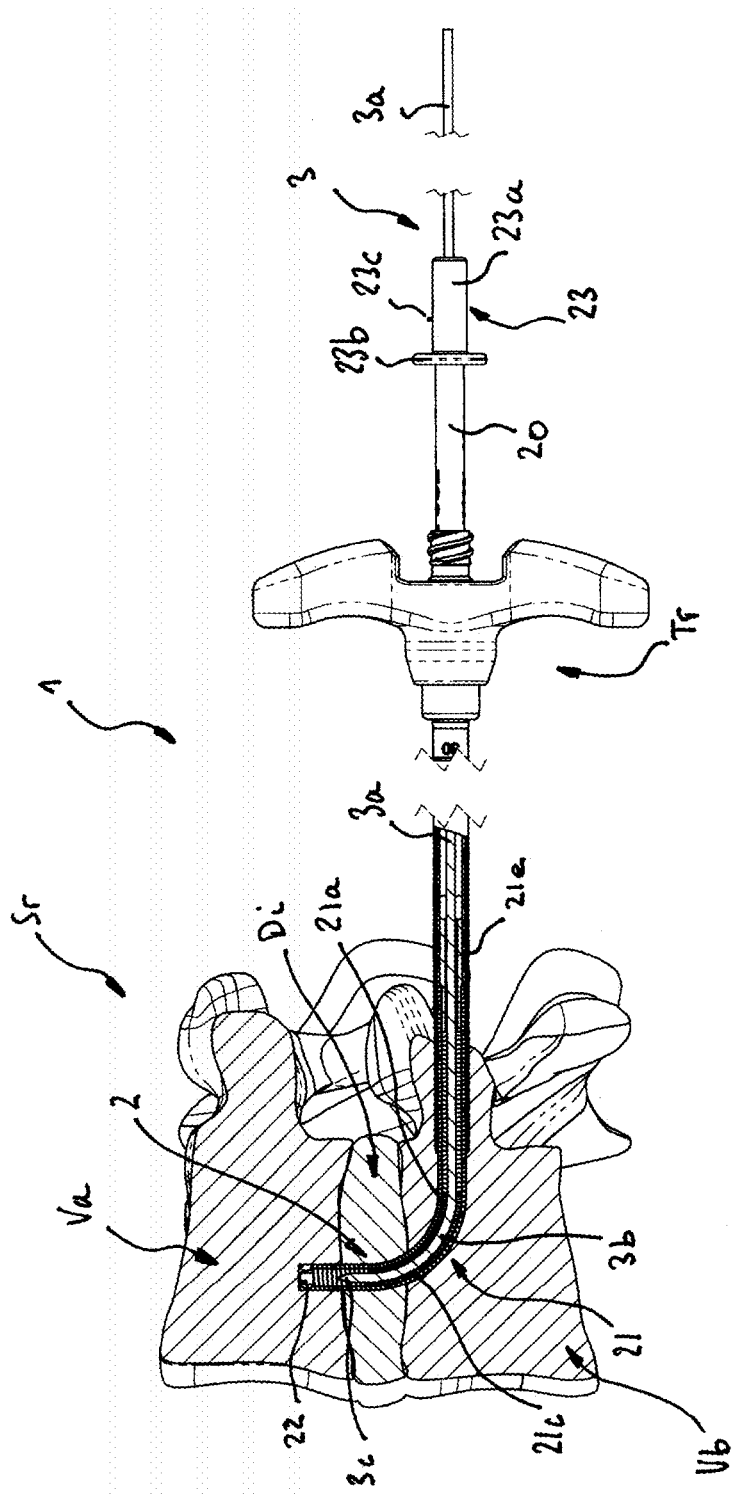
FIG. 1 is a view in section illustrating a segment of spine the bone tissue or connective tissue of which is drilled and/or milled using the flexible and fluted cutting device according to the present invention.
Figure 2:
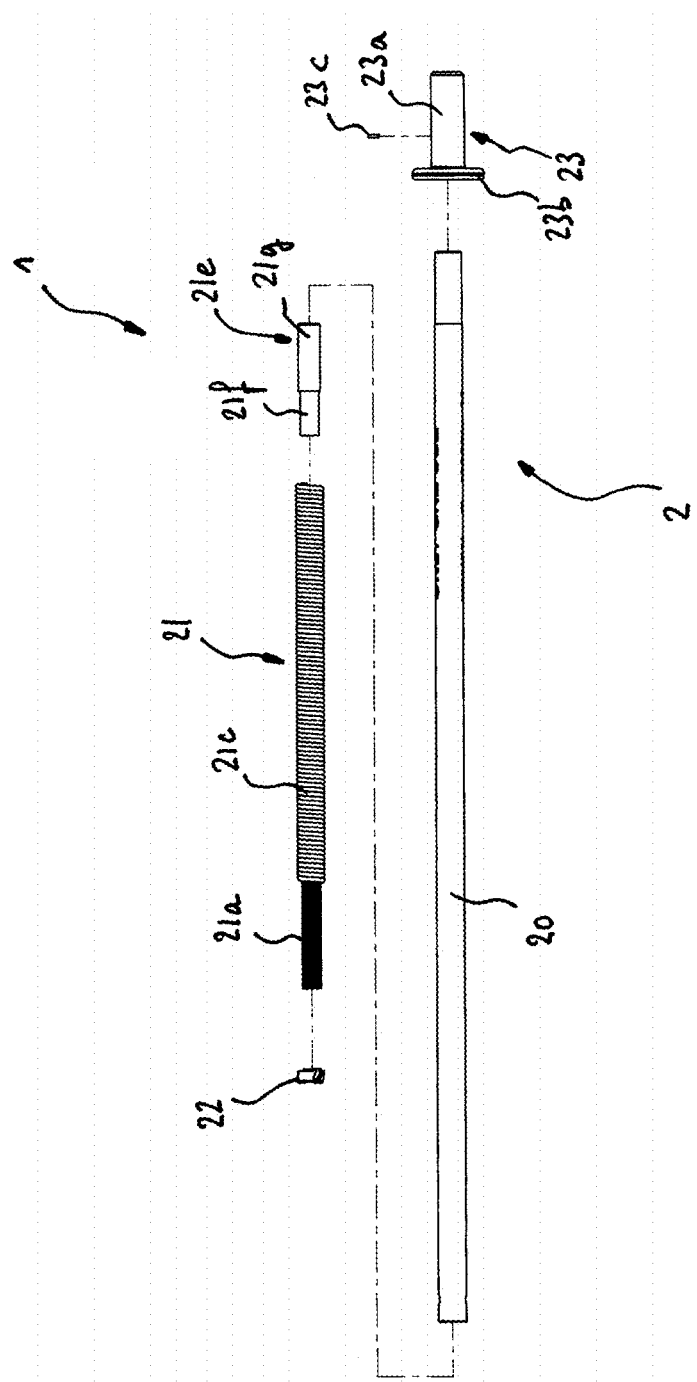
FIG. 2 is an exploded perspective view showing the various components that make up the cutting element of the flexible and fluted cutting device according to the present invention.
Figure 3:
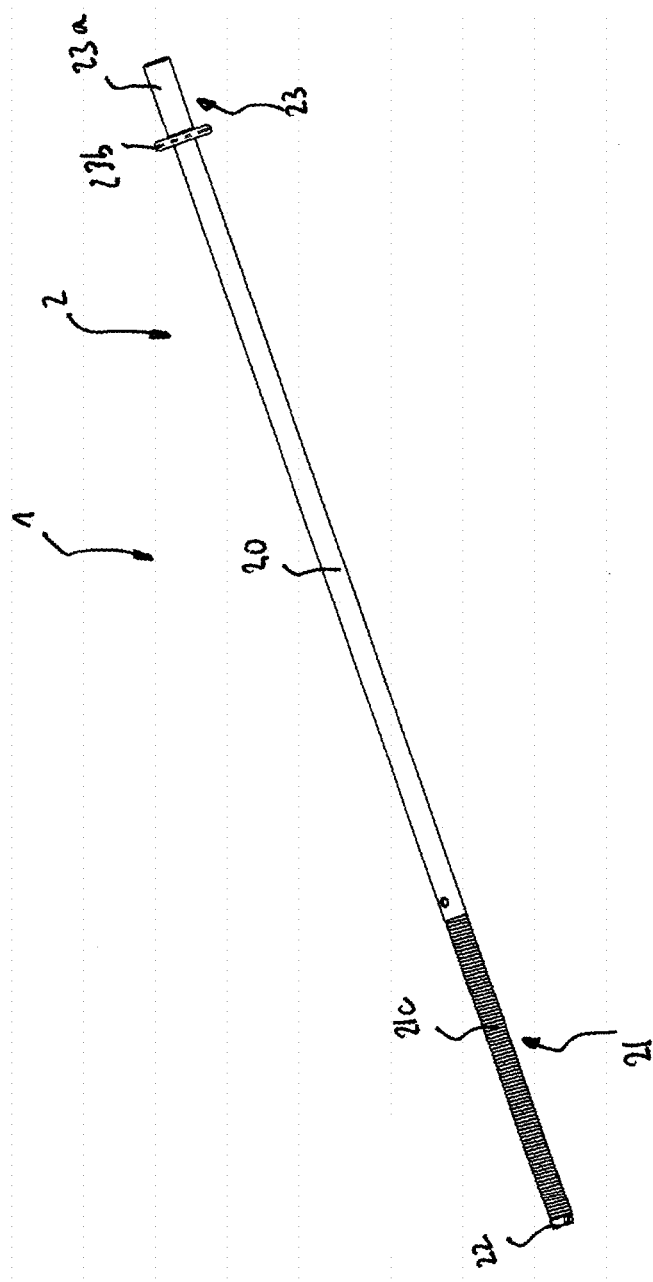
FIG. 3 is a perspective view depicting the assembled cutting element of the flexible and fluted cutting device according to the present invention.
Figure 4:
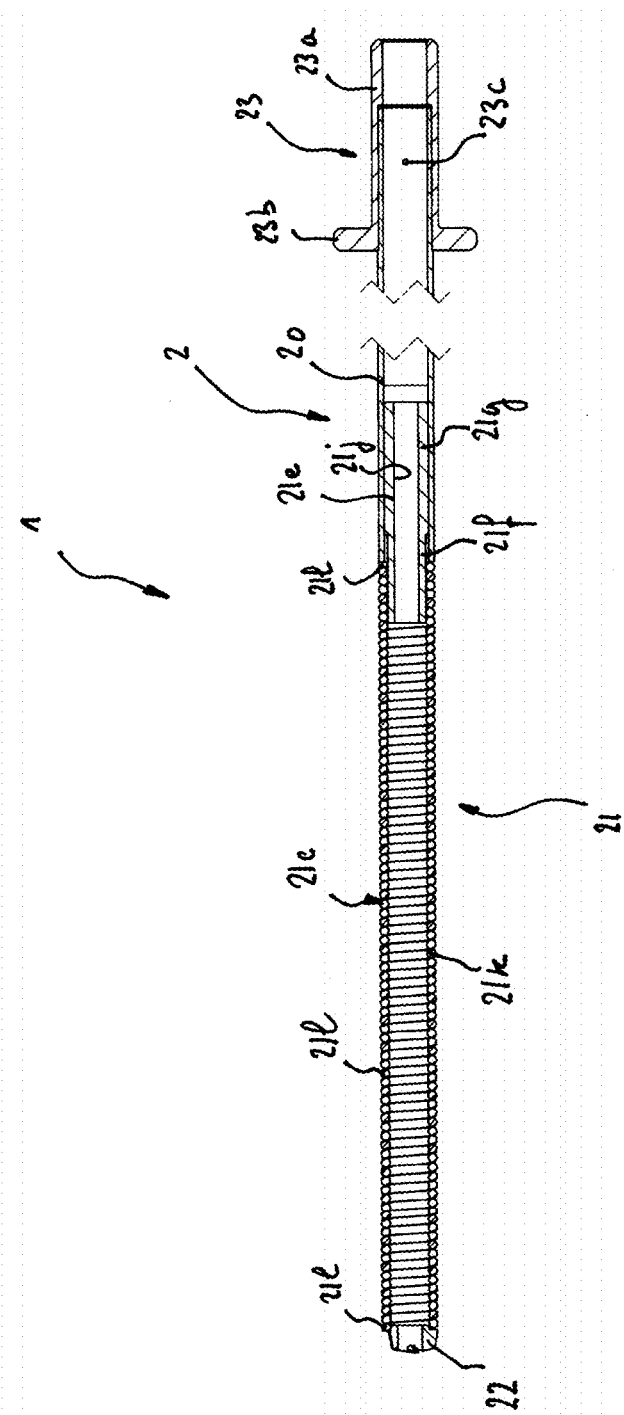
FIG. 4 is a view in section illustrating in detail the arrangement of the supple connection of the cutting element of the flexible and fluted cutting device according to the present invention.
Figure 5:
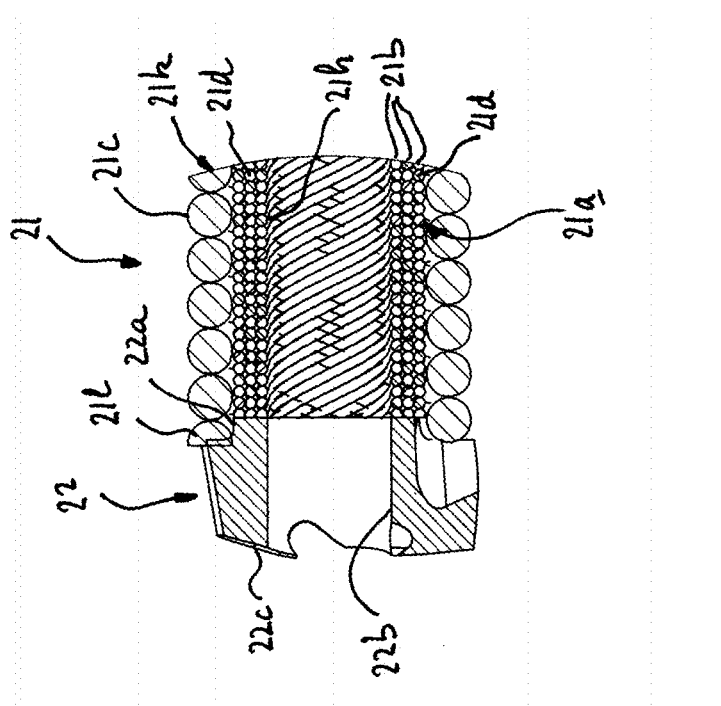
FIG. 5 is a view in section depicting the attachment of the supple connection of the cutting element at the level of the fluted cutter of the flexible and fluted cutting device according to the present invention.
Figure 6:
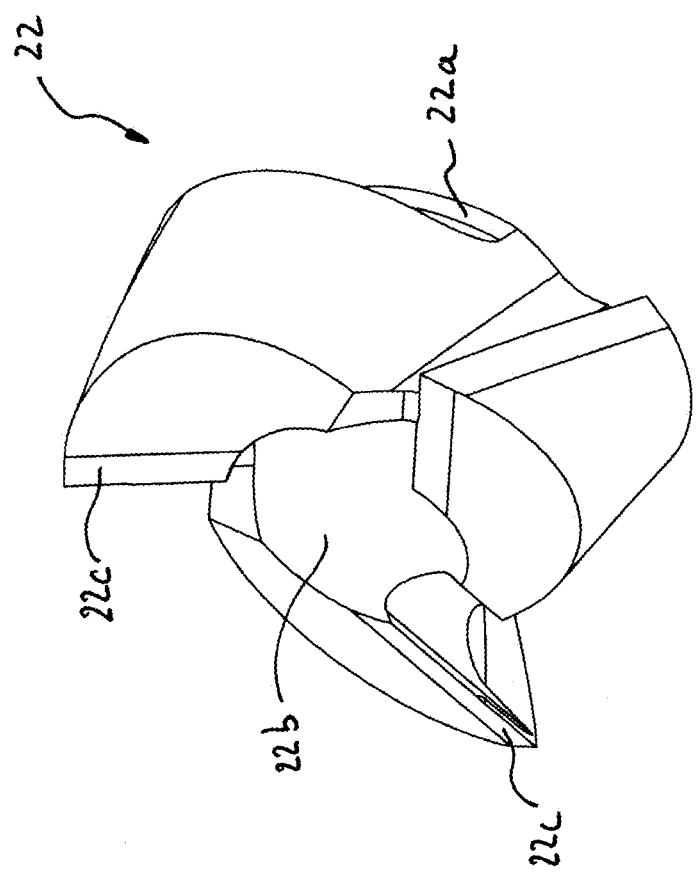
FIG. 6 is a perspective view showing the profile of the fluted cutter of the flexible and fluted cutting device according to the present invention.

FIG. 1 shows a segment of spine Sr of a spinal column of which the vertebrae Va, Vb and the intervertebral disk Di are drilled and/or milled by a flexible and fluted cutting device 1 according to the present invention.

Prior to the placement of the cutting device 1, a straight trocar Tr is anchored for example in the lower vertebra Vb, to guide said cutting device 1 in the straight and horizontal part of the drilling of said vertebra Va.

The cutting device 1 is made up of a flexible and fluted cutting element 2 and of a guide element 3 with a curved profile providing the positioning and angular deformation of the cutting element 2 within the bone tissue and/or connective tissue.

The guide element 3 of the cutting device 1 is made up of a rod 3a made of Nitinol having a small diameter and an end with a curved profile 3b of predetermined radius ending in a tapered point 3c.

The guide element 3 is made of a hyperelastic material ensuring elastic deformation of the end with a curved profile 3b so as to allow it to be introduced into the straight trocar Tr.

The flexible and fluted cutting element 2 of the cutting device 1 is made up of a rigid tube 20 secured at one of its ends to a supple and flexible connection 21 extended by a fluted cutter 22 and at the opposite end to a safety connector 23 allowing connection with drive means which have not been depicted.

The supple and flexible connection 21 is made up of a hollow strand 21a with helicoidal fibers or threads 21d around which a protective sheath 21c is arranged, these being respectively assembled with the fluted cutter 22 on the one hand and with the rigid tube 20 on the other.

The hollow strand 21a is made up of an arrangement of at least three layers 21b of helicoidal fibers or threads 21d arranged in a staggered configuration delimiting an internal bore 21h.

Each layer 21b is formed of at least eighteen fibers or threads 21d arranged evenly at the circular periphery of the strand 21a in a helical profile along the longitudinal axis of said strand.

The first and third layers 21b are arranged along the longitudinal axis of the strand 21a in one and the same first helical direction, whereas the second layer 21b interposed between the first and the third is directed in a second helical direction that intersects said first helical direction.

Each fiber or thread 21d of each layer 21b of the hollow strand 21a has the same outside diameter.

The hollow strand 21a collaborates at one of its ends with the vertical edge of a first cylindrical part 21f of a tubular spacer 21e to which the free ends of the helical fibers or threads 21d of the three layers 21b arranged in a staggered configuration are welded.

The hollow strand 21a is positioned in the continuation of the first cylindrical part 21f of the spacer 21e so that the internal bores 21h and 21l are respectively coaxial.

The spacer 21e comprises, in the continuation of the first cylindrical part 21f, a second cylindrical part 21g of which the outside diameter is greater than that of said first so as to collaborate with the internal bore of the rigid tube 20.

The second cylindrical part 21g of the spacer 21e is prevented from translational and rotational movement inside the rigid tube 20 by any fixing means such as, for example, by welding and/or by axial deformation of the external wall of said tube.

The other free ends of the helicoidal fibers or threads 21d of the three layers 21b arranged in a staggered configuration of the hollow strand 21a which are the opposite ends to the ones secured to the spacer 21e are fixed by welding to the vertical edge of a shoulder 22a of the fluted cutter 22.

The hollow strand 21a is positioned with respect to the fluted cutter 22 in such a way that the internal bores 21h and 22b are respectively in the continuation of one another.

The protective sheath 21c of the supple and flexible connection 21 is made up of a spring 21k with contiguous turns 21l enveloping the external face of the helicoidal fibers or threads 21d of the hollow strand 21a and of which each end is respectively secured to the rigid tube 20 and to the fluted cutter 22.

In this exemplary embodiment, the first free end of the spring 21k is secured to the rigid tube 20 by welding the first turn 21l to the vertical edge of the free end of said tube.

The second free end of the spring 21k is secured to the fluted cutter 22 by welding the last turn 21l to the external periphery of the shoulder 22a near the region at which the hollow strand 21 is secured to this same shoulder.

In an alternative form of embodiment, the protective sheath 21c may be made up of a supple polymer sheath of which each end may be fixed directly or indirectly to the rigid tube 20 and the fluted cutter 22.

The fluted cutter 22 of the flexible cutting element 2 has at least three teeth 22c evenly distributed about an internal bore 22b and of which the cutting profile respectively removes waste material causing, when the cutting device 1 is rotationally driven, it to advance into the bone tissue or connective tissue.

The fluted and waste-removing cutter 22 makes it possible to reduce the compressive stresses transmitted to the supple and flexible connection 21 during boring or milling. The cutting angles of the teeth 22c are suited to reducing the axial compressive loads when removing bone tissue or connective tissue.

The safety connector 23 of the flexible and fluted cutting element 2 has a rupture torque which is lower than the rupture torque of the supple and flexible connection 21 to the rigid tube 20 ensuring that said cutting device 1 is uncoupled from the drive means when the fluted cutter 22 encounters dense tissue leading to an increase in the resistive torque.

The safety connector 23 is made up of a cylindrical sleeve 23a secured at one of its ends to a flange 23b. The sleeve 23a has an internal diameter that allows it to accommodate the external diameter of the rigid tube 20.

The safety connector 23 is secured to the rigid tube 20 by means of a pin 23c passing through the sleeve 23a and said tube. The pin 23c is rated to break under a torque which is lower than that of the supple and flexible connection 21 to the rigid tube 20.

It will be appreciated that, in order to avoid breakage of the supple and flexible connection 21 within the body of the patient, breakage is limited by a maximum torque that the pin 23c can withstand, which pin is engineered to break before said supple and flexible connection 21 does.

The structural arrangement of the flexible and fluted cutting element 2 and the way in which the ends of the supple and flexible connection 21 are fixed to the rigid tube 20 and to the fluted cutter 22 ensures, on the one hand, that the hollow strand 21a transmits the torque even along the curved guide element 3 and on the other hand that the protective sheath 21c withstands the axial and radial loadings without breaking.

It should moreover be understood that the foregoing description has been given solely by way of example and that it does not in any way limit the scope of the invention which would not be overstepped if the embodiment details described were replaced by any other equivalent.

The invention claimed is:

1. A flexible and fluted cutting device for drilling and/or milling a space in bone tissue or connective tissue, said device comprising:
    a safety connector (23) allowing connection to a drive, the safety connector (23) for uncoupling said cutting device from the drive;
    a supple and flexible connection (21) extended by a fluted cutter (22),
    the supple and flexible connection (21) comprising
    i) a hollow strand (21a) comprised of helicoidal fibers or threads (21d), the hollow strand (21a) comprising an arrangement of at least three layers (21b) of the helicoidal fibers or the threads (21d) arranged in a staggered configuration delimiting an internal bore (21h), the helicoidal fibers or the threads being respectively assembled with the fluted cutter (22) and with the rigid tube (20), and
    ii) a protective sheath (21c) arranged around the hollow strand (21a);
    a cutting element (2) made up of a rigid tube (20) having a first end and an opposite second end,
    the rigid tube being secured at the first end to the supple and flexible connection (21) extended by a fluted cutter (22) and at the opposite second end to the safety connector (23) for uncoupling said cutting device; and
    a guide element (3) providing positioning and angular deformation of the cutting element (2) within the bone tissue or connective tissue.

2. The flexible and fluted cutting device according to claim 1, wherein each layer (21b) is formed of at least eighteen of the fibers or the threads (21d) arranged evenly at a circular periphery of the strand (21a) in a helical profile along a longitudinal axis of said strand.

3. The flexible and fluted cutting device according to claim 1, wherein first and third layers (21b) of the three layers (21b) are arranged along the longitudinal axis of the strand (21a) in one and the same first helical direction, whereas a second layer (21b) of the three layers (21b) is interposed between the first and the third layer and is directed in a second helical direction that intersects said first helical direction.

4. The flexible and fluted cutting device according to claim 1, wherein the hollow strand (21a) is fixed at one end to a vertical edge of a first cylindrical part (21f) of a tubular spacer (21e) secured to the rigid tube (20) whereas the other end is assembled with a vertical edge of a shoulder (22a) of the fluted cutter (22).

5. The flexible and fluted cutting device according to claim 1, wherein the protective sheath (21c) of the supple and flexible connection (21) is made up of a spring (21k) with contiguous turns (21l) enveloping an external face of the helicoidal fibers or threads (21d) of the hollow strand (21a) and of which each end is respectively secured to the rigid tube (20) and to the fluted cutter (22).

6. The flexible and fluted cutting device according to claim 1, wherein the protective sheath (21c) is comprised of a supple polymer sheath of which each end is fixed directly or indirectly to the rigid tube (20) and the fluted cutter (22).

7. The flexible and fluted cutting device according to claim 1, wherein the fluted cutter (22) of the flexible cutting element (2) has at least three teeth (22c) evenly distributed about an internal bore (22b) and of which a cutting profile respectively removes waste material causing, when said cutting device (1) is rotationally driven, said cutting device (1) to advance into the bone tissue or connective tissue.

8. The flexible and fluted cutting device according to claim 1, wherein the safety connector (23) is secured to the rigid tube (20) via a pin (23c) rated to break under a torque which is lower than that of the supple and flexible connection (21) to said rigid tube (20).

9. The flexible and fluted cutting device according to claim 1, wherein the guide element (3) is made up of a rod (3a) made of Nitinol having an end with a curved profile (3b) of a predetermined radius ending in a tapered point (3c).

10. The flexible and fluted cutting device according to claim 1,
    wherein the protective sheath (21c) of the supple and flexible connection (21) is made up of a spring (21k) with contiguous turns (21l) enveloping an external face of the helicoidal fibers or threads (21d) of the hollow strand (21a) and of which each end is respectively secured to the rigid tube (20) and to the fluted cutter (22), the spring (21k) being arranged around all of the exterior face of the hollow strand (21a) and extending over an exterior surface of the first end of the rigid tube (20), and
    wherein the guide element (3) comprises a rod (3a) having an end with a curved profile (3b) of a predetermined radius ending in a tapered point (3c), the rod (3a) being located within the internal bore (21h) and extending from the first end of the rigid tube (20) to the second end of the rigid tube (20).

11. A flexible and fluted cutting device for drilling and milling a space in bone tissue or connective tissue, said device comprising:
    a cutting element (2) comprising a rigid tube (20) having a first end and an opposite second end;
    a supple and flexible connection (21) secured to the first end of the rigid tube (20), the supple and flexible connection (21) extended by a fluted cutter (22),
    the supple and flexible connection (21) comprising
    i) a hollow strand (21a) being comprised of at least three layers (21b) of helicoidal fibers, the at least three layers (21b) of the helicoidal fibers (21d) being arranged in a staggered configuration delimiting an internal bore (21h), and
    ii) a protective sheath (21c) arranged around all of an exterior face of the hollow strand (21a) and extending over an exterior surface of the first end of the rigid tube (20);
    a safety connector (23) secured to the second end of the rigid tube (20), the safety connector (23) allowing connection to a drive and allowing for uncoupling said cutting device from the drive; and
    a guide element (3) centrally located within the internal bore (21h) and extending from the first end of the rigid tube (20) to the second end of the rigid tube (20), the guide element (3) providing positioning and angular deformation of the cutting element (2) within the bone tissue or connective tissue.

12. The flexible and fluted cutting device according to claim 11, wherein each layer (21b) is formed of at least eighteen of the helicoidal fibers (21d) arranged evenly at a circular periphery of the hollow strand (21a) in a helical profile along a longitudinal axis of said hollow strand.

13. The flexible and fluted cutting device according to claim 11, wherein first and third layers (21b) of the three layers (21b) are arranged along the longitudinal axis of the strand (21a) in one and the same first helical direction, and a second layer (21b) of the three layers (21b) is interposed between the first layer and the third layer and is directed in a second helical direction that intersects said first helical direction.

14. The flexible and fluted cutting device according to claim 11, wherein the hollow strand (21a) is fixed at one end to a vertical edge of a first cylindrical part (21f) of a tubular spacer (21e) secured to the rigid tube (20) and the other end of the hollow strand comprises a vertical edge of a shoulder (22a) of the fluted cutter (22).

15. The flexible and fluted cutting device according to claim 11, wherein the protective sheath (21c) comprises a spring (21k) with contiguous turns (21l) enveloping an external face of an outer layer of the helicoidal fibers (21d) of the hollow strand (21a), and each end of the spring (21k) is respectively secured to the rigid tube (20) and to the fluted cutter (22), a diameter of each turn of the spring (21k) being greqater than a diameter of the helicoidal fibers, the spring (21k) being arranged around all of the exterior face of the hollow strand (21a) and extending over an exterior surface of the first end of the rigid tube (20).

16. The flexible and fluted cutting device according to claim 11, wherein the protective sheath (21c) is comprised of a supple polymer sheath of which each end is fixed to the rigid tube (20) and the fluted cutter (22).

17. The flexible and fluted cutting device according to claim 11, wherein the fluted cutter (22) has at least three teeth (22c) evenly distributed about an internal bore (22b) and of which a cutting profile respectively removes waste material causing, when said cutting device (1) is rotationally driven, said cutting device (1) to advance into the bone tissue or connective tissue.

18. The flexible and fluted cutting device according to claim 11, wherein the safety connector (23) is secured to the rigid tube (20) via a pin (23c) rated to break under a torque which is lower than that of the supple and flexible connection (21) to said rigid tube (20).

19. The flexible and fluted cutting device according to claim 11, wherein the guide element (3) is made up of a rod (3a) made of Nitinol having an end with a curved profile (3b) of a predetermined radius ending in a tapered point (3c).

* * * * *